US008524873B2

(12) United States Patent
Manabe et al.

(10) Patent No.: US 8,524,873 B2
(45) Date of Patent: Sep. 3, 2013

(54) SUGAR DONOR

(75) Inventors: Shino Manabe, Tokyo (JP); Yukishige Ito, Tokyo (JP); Kazuyuki Ishii, Tokushima-ken (JP)

(73) Assignee: Riken, Saitama (JP)

( * ) Notice: Subject to any disclaimer, the term of this patent is extended or adjusted under 35 U.S.C. 154(b) by 57 days.

(21) Appl. No.: 11/680,248

(22) Filed: Feb. 28, 2007

(65) Prior Publication Data

US 2007/0208171 A1 Sep. 6, 2007

(30) Foreign Application Priority Data

Mar. 2, 2006 (JP) ................................ 2006-055774

(51) Int. Cl.
*C07G 3/00* (2006.01)
*C07H 1/00* (2006.01)

(52) U.S. Cl.
USPC ......................................... 536/4.1; 536/1.11

(58) Field of Classification Search
USPC ................................................ 536/1.11, 4.1
See application file for complete search history.

(56) References Cited

PUBLICATIONS

Kerns, R.J., Zha, C., Benakli, K., Liang, Y.-Z. (2003) Extended applications and potential limitations of ring-fused 2,3-oxazolidinone thioglycosides in glycoconjugate synthesis. Tetrahedron Letters, vol. 44, p. 8069-8072.*
Hanessian, S. (1997) "Glycoside Synthesis Based on the Remote Activation Concept: An Overview" in the Preparative Carbohydrate Chemistry, editor Stephen Hanessian, published by Marcel Dekker, Inc., p. 381-383.*
Greene, T.W. and Wuts, P.G.M. (1991) Protective Groups in Organic Synthesis, published by John Wiley & Sons, Inc., p. 4 and 89-93.*
Banoub, J., Boullanger, P., Lafont, D. (1992) Synthesis of Oligosaccharides of 2-Amino-2-deoxy Sugars. Chemical Reviews, vol. 92, p. 1167-1195.*
Kroutil, J., Trnka, T., Cerny, M. (2000) Selective N-Debenzylation of Benzylamino Derivatives of 1,6-Anhydro-β-D-hexopyranoses. Organic Letters, vol. 2, No. 12, p. 1681-1683.*
Bull, S.D., Davies, S.G., Fenton, G., Mulvaney, A.W., Prasad, R.S., Smith, A.D. (2000) Chemoselective debenzylation of N-benzyl tertiary amines with ceric ammonium nitrate. Journal of the Chemical Society, Perkins Transactions 1, p. 3765-3774.*
Boysen, M., Gemma, E., Lahmann, M., Oscarson, S. (2005) Ethyl 2-acetamido-4,6-di-O-benzyl-2,3-N,O-carbonyl-2-deoxy-1-thio-β-D-glycopyranoside as a versatile GlcNAc donor. Chemical Communications, p. 3044-3046.*
Wei, P., Kerns, R.J. (2005) Factors Affecting Stereocontrol duriing Glycosidation of 2,3-Oxazolidinone-Protected 1-Tolythio-n-acetyl-D-glucosamine. Journal of Organic Chemistry, vol. 70, p. 4195-4198.*
S. Manabe et al.; Journal of the American Chemical Society, 2006, vol. 128, pp. 10666-10667.
P. Wei et al., J. Org. Chem.; 2005, vol. 70, pp. 4195-4198.
Satoh et al., "Low-Barrier Pathway for *endo*-Cleavage Induced Anomerization of Pyranosides with N-Benzyl-2,3-*trans*-oxazolidinone Groups" *Eur. J. Org. Chem.*, pp. 1127-1131, 2009.
Olsson et al., "Investigations of Glycosylation Reactions with 2-N-Acetyl-2N,3O-oxazolidinone-Protected Glucosamine Donors" *J. Org. Chem.*, vol. 73, No. 18, pp. 7181-7188, 2008.
Manabe et al., "Evidence for Endocyclic Cleavage of Conformationally Restricted Glycopyranosides" *Chem. Eur. J.*, vol. 15, pp. 6894-6901, 2009.
Manabe et al., "Significant Solvent Effect in Anomerization Reaction of Pyranosides with 2,3-*trans* Carbamate and Carbonate" *Tetrahedron Letters*, vol. 50, pp. 4827-4829, 2009.
Benakli et al., "Oxazolidinone Protected 2-Amino-2-deoxy-D-glucose Derivatives as Versatile Intermediates in Stereoselective Oligosaccharide Synthesis and the Formation of α-Linked Glycosides" *J. Am. Chem. Soc.*, vol. 123, No. 38, pp. 9461-9462, published online Sep. 1, 2001.
Japanese Office Action that issued with respect to patent family member Japanese Patent Application No. 2006-055774, mailed Apr. 17, 2012.

* cited by examiner

*Primary Examiner* — Scarlett Goon
(74) *Attorney, Agent, or Firm* — Greenblum & Bernstein, P.L.C.

(57) ABSTRACT

The present invention provides a compound represented by the following formula (1):

$$\text{(1)}$$

wherein X1 and X2 each independently represent a hydrogen atom or a hydroxyl-protecting group; Y represents a C7-20 aralkyl group which may optionally have one or more substituents selected from a halogen atom, a lower alkyl group or a lower alkoxy group; and Z represents a halogen atom, a C1-4 alkylthio, or an arylthio group, or its corresponding sulfoxide group.

5 Claims, 2 Drawing Sheets

Scheme 1.

Scheme 2.

SUGAR DONOR

TECHNICAL FIELD

The present invention relates to a novel compound that is useful as a sugar donor in sugar chain synthesis reaction. More particularly, the present invention relates to a novel compound that is useful as a sugar donor in the 1,2-cis-glucosylation reaction.

BACKGROUND ART

General oligosaccharide synthesis can be performed only when stereoselective glycosylation is possible. In general, the anomeric position can be selected by optimizing reaction conditions, such as solvent, temperature, promoter, leaving group, and protecting group patterns. At present, stereoselective synthesis of 1,2-cis-glycoside is a complicated oligosaccharide synthesis challenge. Concerning proceeding of the 1,2-cis-stereoselective glycosylation of 2-amino-2-deoxysugar, in particular, Lemieux and Paulsen reported about 30 years ago the introduction of an azide group into position 2 as a protecting group that is not involved with an adjacent group (H. Paulsen, et al., Chem. Ber., 1978, 111, 2358-2369 and R. U. Lemiuex, et al., Can. J. Chem., 1979, 57, 1244-1251). According to the method of Lemieux and Paulsen, the 1,2-cis-form is preferentially synthesized, but satisfactory selectivity is not always realized. Also, sugar donor synthesis disadvantageously involves the employment of a special technique referred to as azidonitration, or the use of triflic azide, which causes danger of explosion.

In 2001, Kerns reported that a sugar donor having 2,3-trans-oxazolidinone exhibited high selectivity (K. Benakli, et al., J. Am. Chem. Soc., 2001, 123, 9461-9462). However, this sugar donor is reported to have several drawbacks (P. Wei, et al., J. Org. Chem., 2005, 70, 4195-4198 and P. Wei, et al., Tetrahedron Lett. 2005, 46, 6901-6905). First of all, at least 2 equivalent amounts of activators (phenylsulfenyl triflate) are required. Also, sulfenylation and glycosylation at nitrogen atom are severe side reactions. When a nitrogen atom is subjected to acetylation, selectivity is significantly decreased, although β-selectivity is occasionally observed. In the case of a sugar donor using an acetamide group as an amino-protecting group, deprotection of trans-oxazolidinone at 2,3-positions is problematic under basic conditions. That is, hydrolysis of the trans-oxazolidinone structure is intended while maintaining an acetamide group. However, such hydrolysis disadvantageously competes with acetamide hydrolysis, which makes performance of selective hydrolysis difficult and which results in formation of various products in some cases.

DISCLOSURE OF THE INVENTION

An object of the present invention is to overcome the problems of the prior art techniques described above. Specifically, the present invention provides a sugar donor compound that is capable of performing stereoselective 1,2-cis-glycosylation.

The present inventors have conducted concentrated studies in order to attain the above object. As a result, they developed a simple method for synthesizing a novel 2,3-trans-oxazolidinone derivative and discovered that the product was useful as a sugar donor in the 1,2-cis-glycosylation reaction. Further, they also discovered that deprotection reaction could be easily carried out. The present invention has been completed based on these findings.

Thus, the present invention provides a compound represented by the following formula (1):

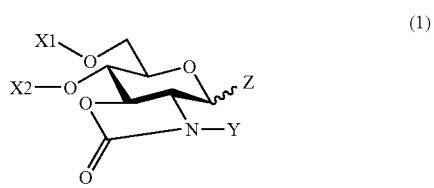

wherein X1 and X2 each independently represent a hydrogen atom or a hydroxyl-protecting group; Y represents a C7-20 aralkyl group which may optionally have one or more substituents selected from a halogen atom, a lower alkyl group or a lower alkoxy group; and Z represents a halogen atom, a C1-4 alkylthio, or an arylthio group, or its corresponding sulfoxide group.

Preferably, Y represents a benzyl group or p-methoxy benzyl group, and Z represents —$SC_6H_5$.

Preferably, X1 represents a benzyl group, p-methoxy benzyl group, benzoyl group, allyl group, or acetyl group, and X2 represents a chloroacetyl group.

Another aspect of the present invention provides a sugar-donating reagent for sugar chain synthesis which comprises the aforementioned compound of the present invention.

A further aspect of the present invention provides a method for the synthesis of sugar chain which comprises a step of allowing the aforementioned compound of the present invention to react with and bind to a sugar receptor.

PREFERRED EMBODIMENTS OF THE INVENTION

Figure 1:
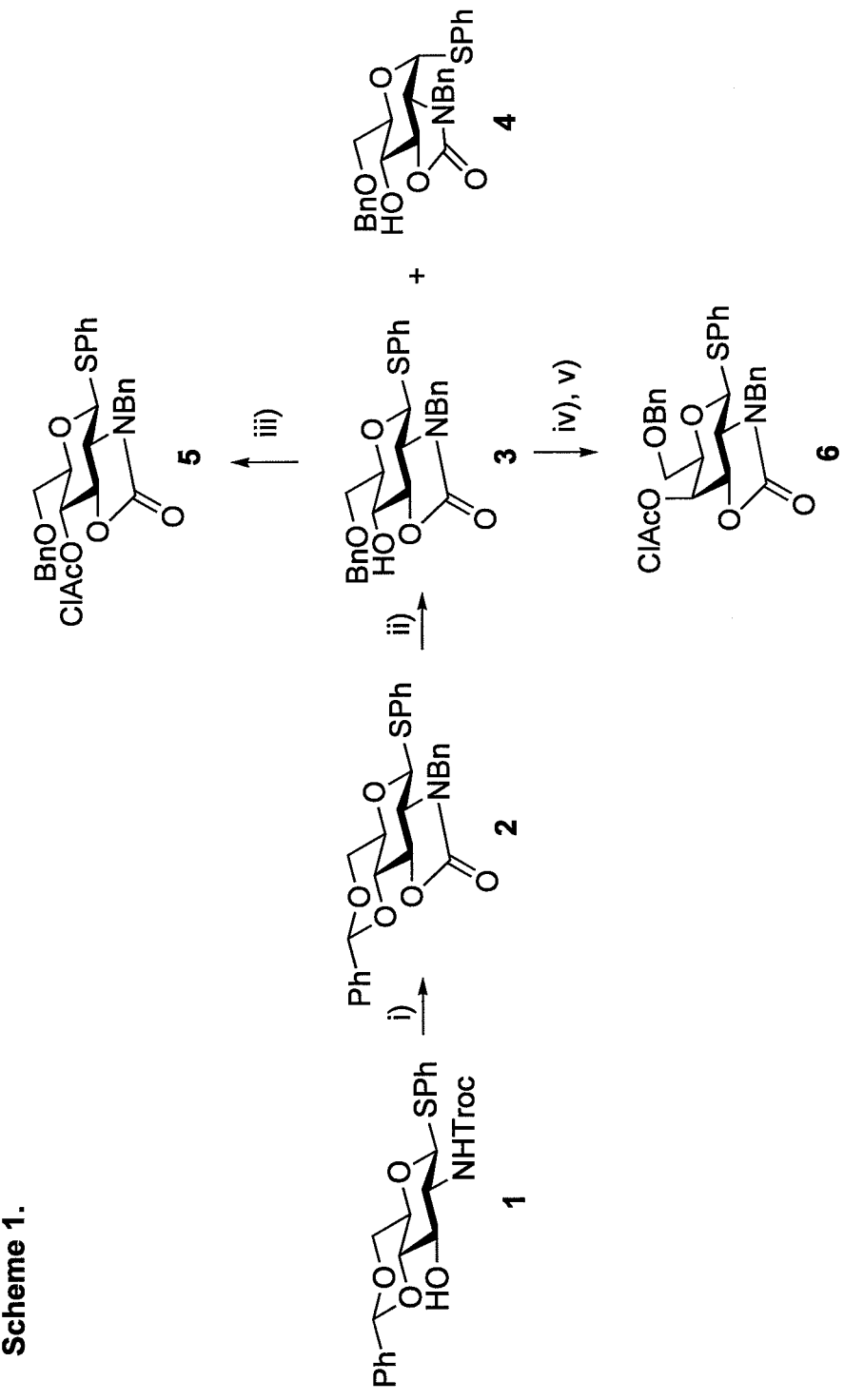
FIG. 1 shows the synthesis of donors (Compounds 5 and 6).
Figure 2:
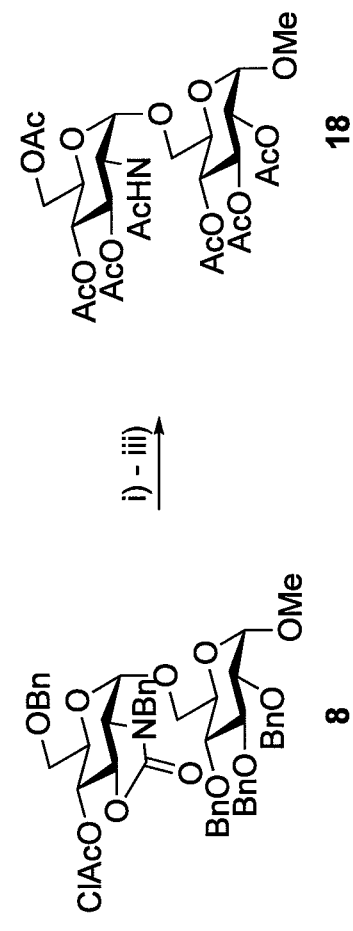
FIG. 2 shows the synthesis of a disaccharide (Compound 18).

At the outset, the present invention is described in accordance with the examples of the present invention with reference to Table 1 and FIGS. 1 and 2.

The compound of the present invention is a novel sugar donor used for 1,2-cis glycosylation of 2-amino-2-deoxysugar. Sugar donors (Compounds 5 and 6) each comprise 2,3-trans-oxazolidinone having an N-benzyl group. Synthesis of donors (Compounds 5 and 6) is shown in FIG. 1. Specifically, GlcNAc (Compound 1) protected with trichloroethyl carbamate (K. Benakli, et al., J. Am. Chem. Soc. 2001, 123, 9461-9462) was converted into 2,3-trans-oxazolidinone derivative (Compound 2) using BnBr and NaH in a single process with a yield of 96% (FIG. 1). Under general ring opening conditions of reduced benzylidene acetal using $Et_3SiH$—$BF_3.OEt_2$, Compounds 3 and 4 having free hydroxyl groups at position C-4 were obtained from Compound 2. By subjecting Compound 3 to chloroacetylation, Compound 5 was obtained as a sugar donor. Compound 3 was converted into triflate as an intermediate and then into a galactosamine donor (Compound 6). Stereoselective glycosylation was examined using thioglycosides (Compound 5 and 6).

In the present invention, stereoselectivity was examined using a sugar receptor having a primary alcohol (Compound 7). Under the thioglycoside activation conditions using PhSOTf in combination with N-(phenylthio)-ε-caprolactam- Tf$_2$O, α- and β-products were obtained stereorandomly (Table 1). When the reaction was allowed to proceed in a toluene-dioxane mixture, selectivity was dramatically increased at around room temperature (entry 1, condition C). A galactosamine derivative donor (Compound 6) exhibited slightly higher selectivity under the same reaction conditions (entry 2).

Various sugar receptors were subjected to this method. Complete selectivity was observed in CH$_2$Cl$_2$ under the conditions of Wang in the case of low-reactive 4-OH of glucose (Compound 10) and a glycosamine derivative (Compound 12). Through the 400 MHz $^1$H-NMR analysis following the gel filtration of a crude mixture, β-glycoside was not identified. A low-reactive secondary alcohol exhibited selectivity regardless of solvent. A hydroxyl group at position C-4 of glucosamine is known to have relatively low reactivity. This sugar donor generated a disaccharide (Compound 13) with a high yield. Compounds 15 and 17 are components of heparin which is an agent for preventing and treating thromboembolic diseases. High selectivity was attained in all such cases. A high yield was frequently attained when 1.2 equivalent amounts of sugar donors (Compounds 5 and 6) were used, and side products were rarely generated from sugar donors.

A disaccharide (Compound 8) can be deprotected. Specifically, after deprotecting oxazolidinone under basic conditions, O— and N-benzyl groups were removed via hydrogenation. After an unprotected disaccharide was acetylated, a disaccharide (Compound 18) was obtained (FIG. 2).

The compound of the present invention is represented by following formula (1):

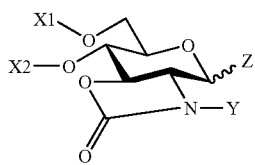

(1)

wherein X1 and X2 each independently represent a hydrogen atom or a hydroxyl-protecting group; Y represents a C7-20 aralkyl group which may optionally have one or more substituents selected from a halogen atom, a lower alkyl group or a lower alkoxy group; and Z represents a halogen atom, a C1-4 alkylthio, or an arylthio group, its corresponding sulfoxide group.

In formula (1), X1 and X2 each independently represent a hydrogen atom or a hydroxyl-protecting group. Examples of hydroxyl-protecting groups include benzyl, chloroacetyl, acetyl, levulinoyl, p-methoxybenzyl, and silyl ether groups. Particularly preferably, X1 represents a benzyl group, and X2 represents a chloroacetyl group.

In formula (1), Y represents a C7-20 aralkyl group which may optionally have one or more substituents selected from a halogen atom, a lower alkyl group or a lower alkoxy group. In general, the lower alkyl group may be a C1-8 alkyl group, and preferably a C1-6 alkyl group. An alkyl group may be a linear, branched, or cyclic group. Examples of a C7-20 aralkyl group include a substituted benzyl group, such as a benzyl, or p-methoxybenzyl group, and an allyl group, with a benzyl group being particularly preferable.

Z represents a halogen atom such as a fluorine, chlorine, bromine or iodine atom, C1-4 alkylthio such as —SCH$_3$ or —SC$_2$H$_3$, or optionally substituted —SC$_6$H$_5$, with —SC$_6$H$_5$ being particularly preferable.

The compound of the present invention described above can be synthesized in accordance with the route of synthesis shown in FIG. 1 and in accordance with the method described above (and the method precisely described in the examples below).

A compound wherein Y represents an optionally substituted C7-20 aralkyl group except for the benzyl group (shown in Examples) can also be synthesized in the same manner as in the case in which Y represents a benzyl group, by converting Compound 1 into Compound 2 using a corresponding bromide compound instead of benzyl bromide.

A compound wherein Z represents a bromine atom or —SCH$_3$ can be synthesized in the same route of synthesis as the one shown in FIG. 1 by using a starting compound which is different from Compound 1 in that —SC$_6$H$_5$ in Compound 1 is replaced with bromine atom or —SCH$_3$.

The aforementioned compound represented by formula (1) of the present invention is useful as a sugar-donating reagent for sugar chain synthesis. Also, a method for synthesizing a sugar chain by allowing the compound represented by formula (1) of the present invention to react with a sugar receptor is within the scope of the present invention. The glycosylation reaction for synthesizing a sugar chain can be carried out under general conditions. Examples of such conditions include, but are not limited to, the methods A, B, and C described in the Examples below. According to the method A, an activated molecular sieves, silver trifluoromethanesulfonate, 2,6-di-tert-butyl-4-methylpyridine, an acceptor, and a donor are mixed, and benzene sulfenyl chloride is added thereto to allow the reaction to proceed. According to the method B, an activated molecular sieves, N-(phenylthio)-ε-caprolactam, DTBMP, a receptor, and a donor are mixed, and Tf$_2$O is added thereto to allow the reaction to proceed. According to the method C, DTBMP, AgOTf, a receptor, a donor, and an activated molecular sieve are mixed, and PhSCl is added thereto to allow the reaction to proceed.

The present invention is hereafter described in greater detail with reference to the following examples, although the technical scope of the present invention is not limited thereto.

EXAMPLES (1) General Procedures

Optical rotations were measured with a JASCO DIP-310 polarimeter. Melting points (not corrected) were measured with a YANACO micro melting point apparatus. $^1$H and $^{13}$C NMR spectra were recorded at ambient temperature (23~24° C.) in CDCl$_3$ using JEOL JNM-ECP 500 MHz NMR spectrometer and JEOL EX-400 (400 MHz). Chemical shifts are reported in ppm relative to internal tetramethylsilane (δ=0.00 ppm) for $^1$H and CDCl$_3$ (δ=77.00 ppm) for $^{13}$C NMR spectra. Silica gel 60N (spherical, neutral, Kanto Chemical Co., Inc, Tokyo) was used for flash column (40-100 μm) and open column (100-200 μm) chromatography. Silica gel 60 F$_{254}$ (E. Merck) was used for analytical and preparative thin-layer chromatography.

(2) Synthesis of Phenyl N-benzyl-2-amino-4,6-O-benzylidene-2-N,3-O-carbonyl-2-deoxy-1-thio-α-D-glucopyranoside (Compound 2)

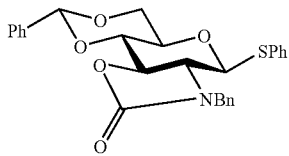

To an ice-cold mixture of trichloroethyl carbamate (compound 1) (2.20 g, 4.11 mmol) and benzyl bromide (0.98 mL, 8.22 mmol) in DMF (40 mL) was added NaH (0.2 g, 8.22 mmol). After stirring the mixture for 30 min on the ice-water bath, the reaction mixture was warmed up to room temperature and stirred for 30 min. The mixture was quenched by addition of $Et_3N$ (1.5 mL), diluted with ethylacetate, poured into saturated aqueous $NH_4Cl$ and extracted with ethylacetate. The combined organic extracts were washed with water and brine, dried ($Na_2SO_4$), filtered and concentrated. The crystalline residue was crystallized from ethylacetate/hexane to give compound 2 (1.88 g, 96%) as a colorless crystal.

MP: 216-217° C. $[\alpha]^{24}_D$ −72 (c, 1.0, $CHCl_3$).

$^1$H NMR (500 MHz, $CDCl_3$) δ: 7.47-7.26 (m, 15 H, aromatic H), 5.59 (s, 1 H, acetal-PhCH), 4.85 (d, $J_{1,2}$=10.0 Hz, 1 H, H-1), 4.83 (d, J=15.5 Hz, 1 H, N—$CH_2$Ph), 4.78 (d, J=15.5 Hz, 1 H, N—$CH_2$Ph), 4.32 (t, $J_{2,3}$=10.5 Hz, 1 H, H-3), 4.32 (dd, $J_{5,6a}$=5.0 Hz, $J_{6a,6b}$=10.5 Hz, 1 H, H-6a), 4.04 (dd, $J_{3,4}$=10.0 Hz, $J_{4,5}$=8.5 Hz, 1 H, H-4), 3.90 (t, $J_{5,6b}$=10.0 Hz, 1 H, H-6b), 3.57 (dddd, 1 H, H-5), 3.52 (dd, $J_{1,2}$=10.0 Hz, $J_{2,3}$=10.5 Hz, 1 H, H-2).

$^{13}$C NMR (125 MHz, $CDCl_3$): δ=158.8 (oxazolidinone, C=O), 136.4, 136.3, 132.6, 131.7, 129.3, 129.2, 128.7, 128.3, 128.0, 127.6, 126.1 (aromatic C), 101.4 (acetal-CHPh), 87.7 (C-1), 78.9 (C-3), 78.4 (C-4), 72.8 (C-5), 68.2 (C-6), 61.5 (C-2), 47.7 (N—$CH_2$Ph).

Anal. Calcd for $C_{27}H_{25}NO_5S$: C, 68.19; H, 5.30; N, 2.95. Found: C, 68.15; H, 5.17; N, 2.88.

(3) Phenyl N-benzyl-2-amino-6-O-benzyl-2-N,3-O-carbonyl-2-deoxy-1-thio-α- and β-D-glucopyranoside (Compounds 3a and 3b)

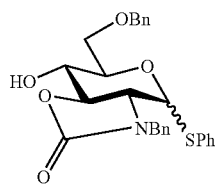

To an ice-cold mixture of compound 2 (7.3 g, 15.4 mmol) and triethylsilane (30 mL, 184.8 mmol) in $CH_2Cl_2$ (200 mL) was added boron trifluoride diethyletherate ($BF_3$·$OEt_2$, 3.9 mL, 30.8 mmol) slowly. After stirring for 80 min at the ice-cold temperature, the mixture was poured into saturated aqueous $NaHCO_3$ and extracted with $CHCl_3$. The combined organic extracts were washed with water, dried ($Na_2SO_4$), filtered and concentrated. Purification of the residue by flash column chromatography on silica gel (3:1->2:1->1:9, $CHCl_3$/ethylacetate) and subsequent crystallization from ethylacetate/hexane gave an α-glycoside (compound 3a) (0.78 g, 11%) and a β-glycoside (Compound 3b) (5.3 g, 72%).

α-Glycoside (Compound 3a)

MP: 118-119° C. $[\alpha]^{22}_D$+210 (c, 1.0, $CHCl_3$).

$^1$H NMR (500 MHz, $CDCl_3$): δ=7.50-7.24 (m, 15 H, aromatic H), 5.37 (d, $J_{1,2}$=4.5 Hz, 1 H, H-1), 4.79 (d, J=15.0 Hz, 1 H, N—$CH_2$Ph), 4.17 (d, J=15.0 Hz, 1 H, N—$CH_2$Ph), 4.60 (d, J=12.0 Hz, 1 H, $CH_2$Ph), 4.50 (d, J=12.0 Hz, 1 H, $CH_2$Ph), 4.36 (dd, $J_{2,3}$=12.0 Hz, $J_{3,4}$=9.5 Hz, 1 H, H-3), 4.14 (dddd, $J_{4,5}$=9.5 Hz, 1 H, H-5), 4.02 (ddd, $J_{H-4,4-OH}$=3.0 Hz, 1 H, H-4), 3.78 (dd, $J_{5,6a}$=4.5 Hz, $J_{6a,6b}$=10.5 Hz, 1 H, H-6a), 3.70 (dd, $J_{5,6b}$=4.0 Hz, 1 H, H-6b), 3.50 (dd, 1 H, H-2), 2.71 (d, 1 H, 4-OH).

$^{13}$C NMR (125 MHz, $CDCl_3$): δ=158.6 (oxazolidinone, C=O), 137.5, 134.4, 132.9, 131.9, 129.1, 129.0, 128.9, 128.5, 128.4, 127.9, 127.7 (aromatic C), 84.9 (C-1), 78.4 (C-3), 73.6 ($CH_2$Ph), 73.0 (C-5), 69.4 (C-4), 68.7 (C-6), 59.6 (C-2), 47.8 (N—$CH_2$Ph).

Anal. Calcd for $C_{27}H_{27}NO_5S$: C, 67.90; H, 5.70; N, 2.93. Found: C, 67.96; H, 5.64; N, 2.85.

β-Glycoside (Compound 3b):

MP: 125-126° C. $[\alpha]^{22}_D$ −77 (c, 1.0, $CHCl_3$).

$^1$H NMR (500 MHz, $CDCl_3$) δ: 7.40-7.22 (m, 15 H, aromatic H), 4.77 (d, $J_{1,2}$=9.0 Hz, 1 H, H-1), 4.74 (s, 2 H, N—$CH_2$Ph), 4.58 (d, J=11.5 Hz, 1 H, $CH_2$Ph), 4.55 (d, J=11.5 Hz, 1 H, $CH_2$Ph), 4.07 (t, $J_{2,3}$=10.5 Hz, 1 H, H-3), 4.01 (dddd, $J_{3,4}$=10.3 Hz, $J_{4,5}$=8.0 Hz, $J_{H-4,4-OH}$=2.5 Hz, 1 H, H-4), 3.79 (dd, $J_{5,6a}$=5.0 Hz, $J_{6a,6b}$=10.0 Hz, 1 H, H-6a), 3.76 (dd, $J_{5,6b}$=5.0 Hz, 1 H, H-6b), 3.56 (dddd, 1 H, H-5), 3.41 (dd, 1 H, H-2), 2.97 (d, 1 H, 4-OH).

$^{13}$C NMR (125 MHz, $CDCl_3$): δ=159.3 (C=O), 137.5, 136.22, 132.4, 132.3, 129.1, 128.6, 128.5, 128.4, 128.2, 127.9, 127.7, 127.6 (aromatic C), 86.7 (C-1), 82.4 (C-3), 79.6 (C-5), 73.7 ($CH_2$Ph), 69.7 (C-6), 69.1 (C-4), 60.1 (C-2), 47.6 (N—$CH_2$Ph).

Anal. Calcd for $C_{27}H_{27}NO_5S$: C, 67.90; H, 5.70; N, 2.93. Found: C, 67.89; H, 5.56; N, 2.84.

(4) Phenyl N-benzyl-2-amino-6-O-benzyl-2-N,3-O-carbonyl-4-O-chloroacetyl-2-deoxy-1-thio-β-D-glucopyranoside (Compound 5)

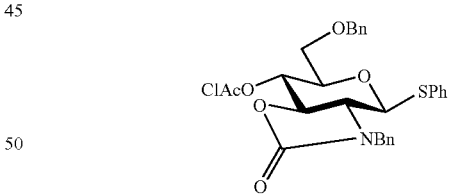

To an ice-cold mixture of 4-OH form (compound 3) (2.6 g, 3.64 mmol) and chloroacetic anhydride (0.94 g, 5.47 mmol) in dichloromethane was added pyridine (0.59 mL, 5.44 mmol). After stirring for 30 min, the mixture was poured into 0.1 M aqueous HCl and extracted with $CHCl_3$. The combined organic extracts were washed with water, dried ($Na_2SO_4$), filtered and concentrated. Purification by column chromatography on silica gel (2:1:1, toluene/hexane/ethylacetate) gave 4-O—ClAc (compound 5) (3.0g, 99%) as a colorless syrup.

$[\alpha]_D^{25}$ −59 (c, 1.0, $CHCl_3$). $^1$H NMR (500 MHz, $CDCl_3$): δ=7.40-7.14 (m, 15 H, aromatic H), 5.37 (dd, $J_{3,4}$=10.5 Hz, $J_{4,5}$=8.5 Hz, 1 H, H-4), 4.80 (d, $J_{1,2}$=9.5 Hz, 1 H, H-1), 4.74 (s, 2 H, N—$CH_2$Ph), 4.55 (d, J=11.5 Hz, 1 H, $CH_2$Ph), 4.47 (d, J=11.5 Hz, 1 H, $CH_2$Ph), 4.18 (t, $J_{2,3}$=11.0 Hz, 1 H, H-3), 3.99

(d, J=15.0 Hz, 1 H, COCH$_2$Cl), 3.91 (d, J=15.0 Hz, 1 H, COCH$_2$Cl), 3.74 (dddd, J$_{5,6a}$=3.5 Hz, J$_{5,6b}$=5.0 Hz, 1 H, H-5), 3.57 (dd, J$_{2,1}$=9.5 Hz, J$_{3,2}$=11.0 Hz, 1 H, H-2).

$^{13}$C NMR (125 MHz, CDCl$_3$): δ=165.8 (COCH$_2$Cl), 158.4 (oxazolidinone, C=O), 137.4, 135.9, 132.5, 132.0, 129.1, 128.7, 128.5, 128.4, 128.2, 127.9, 127,9, 127.8 (aromatic C), 86.8 (C-1), 79.5 (C-3), 78.3 (C-5), 73.6 (CH$_2$Ph), 69.6 (C-4), 68.6 (C-6), 60.1 (C-2), 47.6 (N—CH$_2$Ph), 40.4 (COCH$_2$Cl).

Anal. Calcd for C$_{29}$H$_{28}$ClNO$_6$S: C, 62.87; H, 5.09; N, 2.53. Found: C, 62.71; H, 5.04; N, 2.47.

(5) Phenyl N-benzyl-2-amino-6-O-benzyl-2-N,3-O-carbonyl-4-O-chloroacetyl-2-deoxy-1-thio-α-D-glucopyranoside

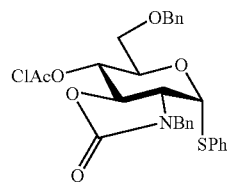

The title compound was prepared in a same manner as described above (99% yield). [α]$^{24}$$_D$ +220 (c, 1.0, CHCl$_3$).

$^1$H NMR (500 MHz, CDCl$_3$) δ: 7.44-7.24 (m, 15 H, aromatic H), 5.41 (d, J$_{1,2}$=5.0 Hz, 1 H, H-1), 5.40 (t, J$_{3,4}$=10.5 Hz, 1 H, H-4), 4.81 (d, J=14.5 Hz, 1 H, N—CH$_2$Ph), 4.17 (d, J=14.5 Hz, 1 H, N—CH$_2$Ph), 4.57 (d, J=11.5 Hz, 1 H, CH$_2$Ph), 4.19 (d, J=11.5 Hz, 1 H, CH$_2$Ph), 4.44 (dd, J$_{2,3}$=12.0 Hz, 1 H, H-3), 4.30 (dddd, J$_{4,5}$=9.5 Hz, J$_{5,6}$=4.0 Hz, 1 H, H-5), 3.97 (d, J=15.0 Hz, 1 H, COCH$_2$Cl), 3.89 (d, J=15.0 Hz, 1 H, COCH$_2$Cl), 3.64 (dd, 1 H, H-2), 3.58 (dd, J$_{6a,6b}$=11.0 Hz, 1 H, H-6a), 3.56 (dd, 1 H, H-6b).

$^{13}$C NMR (125 MHz, CDCl$_3$): δ=165.6 (COCH$_2$Cl), 157.8 (oxazolidinone, C=O), 137.1, 134.1, 132.3, 131.9, 129.3, 129.1, 128.9, 128.6, 128.4, 128.2, 128.1, 128.0 (aromatic C), 84.8 (C-1), 75.8 (C-3), 73.6 (CH$_2$Ph), 71.2 (C-5), 69.9 (C-4), 67.2 (C-6), 59.6 (C-2), 47.9 (N—CH$_2$Ph), 40.3 (COCH$_2$Cl).

Anal. Calcd for C$_{29}$H$_{28}$ClNO$_6$S: C, 62.87; H, 5.09; N, 2.53. Found: C, 62.65; H, 5.05; N, 2.42.

(6) Phenyl N-benzyl-2-amino-4-O-acetyl-6-O-benzyl-2-N,3-O-carbonyl-2-deoxy-1-thio-α- and β-D-glactopyranoside (Compounds 6a and 6b)

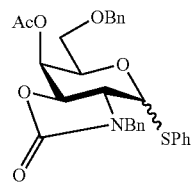

To a mixture of 4-OH form (compound 3) (2.5 g, 5.23 mmol) and pyridine (1.7 mL, 21.0 mmol) in dichloromethane at −40° C. was added trifluoromethanesulfonic anhydride (Tf$_2$O, 1.8 mL, 10.5 mmol) and then the mixture was allowed to warm to −20° C. After stirring for 3 hours, the mixture was poured into 0.1 M aqueous HCl and extracted with CHCl$_3$. The combined organic extracts were washed with saturated aqueous NaHCO$_3$ and water, dried (Na$_2$SO$_4$), filtered and concentrated to dryness. The crude triflate was used for next step without further purification.

The triflate was treated with sodium acetate (4.3 g, 52.3 mmol) in DMF (30 mL) at 60° C. for 2 days. The mixture was diluted with ethylacetate, poured into ice-cold water and extracted with ethylacetate. The combined organic extracts were washed with water and brine, dried (Na$_2$SO$_4$), filtered and concentrated. The residue was purified by silica gel column chromatography (14:1, CHCl$_3$/ethylacetate). A first elution was an α-galactoside (compound 6a) (0.34 g, 13%) and eluted next was a β-galactoside (compound 6b) (2.0 g, 73%). The compounds 6a and 6b were crystallized from ethylacetate/hexane, respectively. α-Galactoside (compound 6a):

MP: 148-149° C. [α]$^{25}$$_D$ +186 (c, 1.0, CHCl$_3$).

$^1$H NMR (500 MHz, CDCl$_3$) δ: 7.40-7.21 (15 H, aromatic H), 5.66 (br. s, 1 H, H-4), 5.40 (d, J$_{1,2}$=4.5 Hz, 1 H, H-1), 4.71 (d, J=15.0 Hz, 1 H, N—CH$_2$Ph), 4.28 (d, J=15.0 Hz, 1 H, N—CH$_2$Ph), 4.56 (dddd, J$_{4,5}$=1.0 Hz, J$_{5,6a}$=5.5 Hz, J$_{5,6b}$=6.0 Hz, 1 H, H-5), 4.49 (dd, J$_{2,3}$=12.5 Hz, J$_{3,4}$=2.5 Hz, 1 H, H-3), 4.49 (d, J=12.0 Hz, 1 H, CH$_2$Ph), 4.43 (d, J=12.0 Hz, 1 H, CH$_2$Ph), 3.97 (dd, 1 H, H-2), 3.56 (dd, J$_{6a,6b}$=10.0 Hz, 1 H, H-6a), 3.51 (dd, 1 H, H-6b), 2.01 (s, 3 H, COCH$_3$).

$^{13}$C NMR (125 MHz, CDCl$_3$) δ: 169.3 (COCH$_3$), 158.0 (oxazolidinone, C=O), 137.5, 134.5, 132.3, 129.1, 129.0, 128.9, 128.4, 128.3, 128.1, 127.8, 127.7 (aromatic C), 85.8 (C-1), 74.2 (C-3), 73.5 (CH$_2$Ph), 70.0 (C-5), 68.3 (C-6), 66.1 (C-4), 56.1 (C-2), 48.2 (N—CH$_2$Ph), 20.6 (COCH$_3$).

Anal. Calcd for C$_{29}$H$_{29}$NO$_6$S: C, 67.03; H, 5.63; N, 2.70. Found: C, 66.78; H, 5.41; N, 2.64.

β-Galactoside (Compound 6b):

MP: 119-120° C. [α]$^{25}$$_D$ −95 (c, 1.0, CHCl$_3$).

$^1$H NMR (500 MHz, CDCl$_3$) δ: 7.40-7.20 (15 H, aromatic H), 5.67 (br. s, 1 H, H-4), 4.78 (d, J=15.5 Hz, 1 H, N—CH$_2$Ph), 4.70 (d, J=15.5 Hz, 1 H, N—CH$_2$Ph), 4.76 (d, J$_{1,2}$=9.5 Hz, 1 H, H-1), 4.52 (d, J=12.0 Hz, 1 H, CH$_2$Ph), 4.42 (d, J=12.0 Hz, 1 H, CH$_2$Ph), 4.21 (dd, J$_{2,3}$=11.5 Hz, J$_{3,4}$=2.0 Hz, 1 H, H-3), 3.93 (br. t, 1 H, H-5), 3.84 (dd, 1 H, H-2), 3.57 (d, J$_{5,6}$=6.0 Hz, 2 H, H-6a and H-6b), 2.04 (s, 3 H, COCH$_3$).

$^3$C NMR (125 MHz, CDCl$_3$) δ: 169.2 (COCH$_3$), 153.6 (oxazolidinone, C=O), 137.5, 136.4, 132.4, 132.2, 129.1, 128.6, 128.4, 128.4, 128.0, 127.8, 127.5 (aromatic C), 88.0 (C-1), 78.9 (C-3), 77.2 (C-5), 73.6 (CH$_2$Ph), 68.1 (C-6), 65.1 (C-4), 57.1 (C-2), 48.1 (N—CH$_2$Ph), 20.6 (COCH$_3$).

Anal. Calcd for C$_{29}$H$_{29}$NO$_6$S: C, 67.03; H, 5.63; N, 2.70. Found: C, 66.95; H, 5.36; N, 2.59.

(7) General Procedure for Glycosylation

Method A: Molecular sieves (MS) 4 Å was activated in vacuo under 170° C. in a two necked round-bottom flask. The flask was purged with argon gas and cooled to room temperature. Silver trifluoromethanesulfonate (AgOTf; 1.5 equiv., based on the donor), 2,6-di-tert-butyl-4-methylpyridine (DTBMP; 2.0 equiv., based on the donor) and a mixture of an acceptor (1 equiv.) and a donor (1.2 equiv.) in CH$_2$Cl$_2$ were added to the flask. Benzenesulfenyl chloride (PhSCl; 1.2 equiv., based on the donor) was added to the mixture at room temperature. After stirring overnight, the mixture was quenched by addition of saturated aqueous NaHCO$_3$ and filtered through Celite. The filter cake was washed with CHCl$_3$ and the filtrates were extracted with CHCl$_3$. The combined organic extracts were washed with water, dried (Na$_2$SO$_4$), filtered and concentrated. The residue was purified by gel permeation chromatography [Biobeads SX-3 (3.0×58 cm, toluene)] and subsequent silica gel column chromatography or preparative TLC to give each glycosylation product shown in Table 1.

Method B: To a mixture of N-(Phenylthio)-ε-caprolactam (1.1 equiv.), DTBMP (2.0 equiv., based on the donor), an acceptor and a donor in CH$_2$Cl$_2$ containing activated MS 4 Å was added Tf$_2$O (1 equiv., based on the donor). After stirring for 0.5~1.5 hour, the mixture was quenched, worked up and purified in a same manner as described for Method A to give each glycosylation product shown in Table 1.

Method C: DTBMP (2.0 equiv., based on the donor), AgOTf (1.5 equiv., based on the donor) and a mixture of an acceptor (1 equiv.) and a donor (1.2 equiv.) in 1,4-dioxane-toluene (3:1, v/v) were added to a flask containing activated MS 4A as described for method A. The mixture was cooled to 0° C., then PhSCl (1.2 equiv., based on the donor) was added. The stirring reaction mixture was allowed to warm to room temperature overnight. The mixture was quenched by addition of saturated aqueous NaHCO$_3$ and filtered through Celite. The filter cake was washed with ethylacetate and the filtrates were extracted with ethylacetate. The combined organic extracts were washed with brine, dried (Na$_2$SO$_4$), filtered and concentrated. The residue was purified in a same manner as described for Method A to give each glycosylation product shown in Table 1.

TABLE 1

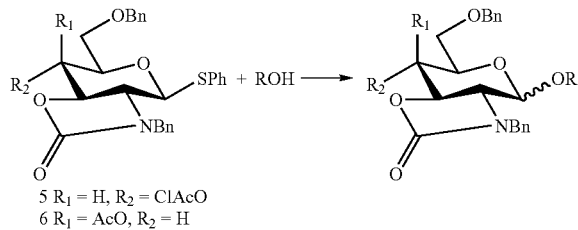

5 R$_1$ = H, R$_2$ = ClAcO
6 R$_1$ = AcO, R$_2$ = H

| entry | donor | ROH | product[1] | conditions | yield (%) α:β |
|---|---|---|---|---|---|
| 1 | 5 | 7 | 8 | A<br>B<br>C | 31:37<br>35:47<br>80:8 |
| 2 | 6 | 7 | 9 | C | 76:5 |
| 3 | 5 | 10 | | B | 52 (α only) |

TABLE 1-continued

| entry | donor | ROH | product[1] | conditions | yield (%) α:β |
|---|---|---|---|---|---|
| 4 | 5 | 12 | 13 | B | 56 (α only) |
| 5 | 5 | 14 | 15 | B / C[2] | 63:4 / 71 (α only) |
| 6 | 5 | 16 | 17 | C | 71:4 |

(8) Methyl(N-benzyl-2-amino-2-N,3-O-carbonyl-4-O-chloroacetyl-2-deoxy-α- and β-D-glucopyranpsyl)-(1->4)-2,3,4-tri-O-benzyl-α-D-glucopyranoside (Compounds 8a and 8b)

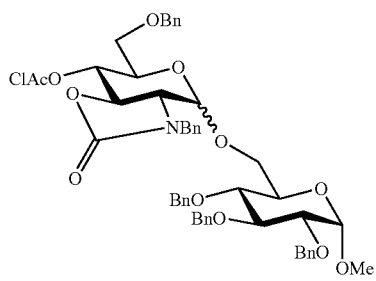

Method A: Compound 7 (23 mg, 0.05 mmol) and compound 5 (33 mg, 0.060 mmol) were dissolved in $CH_2Cl_2$ (3 ml), and the reaction was allowed to proceed at room temperature overnight in the presence of DTBMP (25 mg, 0.120 mmol), AgOTf (23 mg, 0.09 mmol), PhSCl (8 μl, 0.072 mmol), and MS (4 Å, 0.3 g). Subsequent work-up and purification by preparative TLC (toluene/hexane/ethylacetate, 4:1:1) gave compound 8a (14 mg, 31%) and compound 8b (17 mg, 37%).

Method B: Compound 7 (22 mg, 0.047 mmol) and compound 5 (3 mg, 0.056 mmol) were dissolved in $CH_2Cl_2$ (3 ml), and the reaction was allowed to proceed in the presence of N-(phenylthio)-ε-caprolactam (14 mg, 0.062 mmol), $Tf_2O$ (13 μl, 0.074 mmol), and MS (4 Å, 0.3 g) at room temperature for 1.5 hours. The subsequent work-up and purification by preparative TLC (toluene/hexane/ethylacetate, 4:1:1) gave compounds 8a (15 mg, 35%) and 8b (20 mg, 47%).

Method C: Compound 7 (100 mg, 0.215 mmol) and compound 5 (143 mg, 0.258 mmol) were dissolved in 1,4-dioxane/toluene (3:1, 8 ml), and the reaction was allowed to proceed overnight while heating the solution from 0° C. to room temperature in the presence of DTBMP (106 mg, 0.516 mmol), AgOTf (99 mg, 0.387 mmol), PhSCl (36 µl, 0.310 mmol), and MS (4 Å, 0.8 g). The subsequent work-up and purifications by gel permeation chromatography (SX-3) and flash column chromatography on silica gel (CHCl$_3$/toluene/ethylacetate, 10:4:1->10:1:1) gave compounds 8a (143 mg, 76%) and 8b (9 mg, 5%).

α-Linked Disaccharide 8a: $[\alpha]^{26}_D$ +54 (c, 1.0, CHCl$_3$).

$^1$H NMR (500 MHz, CDCl$_3$) δ: 7.83-7.14 (25 H, aromatic H), 5.38 (t, $J^{II}_{4,5}$$^{II}$=10.0 Hz, 1 H, H-4$^{II}$), 5.01 (d, J=11.0 Hz, 1 H, CH$_2$Ph), 4.38 (d, J=11.0 Hz, 1 H, CH$_2$Ph), 4.92 (d, J=11.5 Hz, 1 H, CH$_2$Ph), 4.58 (d, J=11.5 Hz, 1 H, CH$_2$Ph), 4.84 (d, $J^{II}_{1,2}$$^{II}$=3.0 Hz, 1 H, H-1$^{II}$), 4.80 (d, J=12.0 Hz, 1 H, CH$_2$Ph), 4.64 (d, J=12.0 Hz, 1 H, CH$_2$Ph), 4.55 (d, J=14.5 Hz, 1 H, N—CH$_2$Ph), 4.00 (d, J=14.5 Hz, 1 H, N—CH$_2$Ph), 4.51 (d, J=12.0 Hz, 1 H, CH$_2$Ph), 4.35 (d, J=12.0 Hz, 1 H, CH$_2$Ph), 4.50 (d, $J^{I}_{1,2}$=4.0 Hz, 1 H, H-1$^I$), 4.41 (dd, $J^{II}_{2,3}$=12.0 Hz, $J^{II}_{3,4}$=10.5 Hz, 1 H, H-3$^{II}$), 4.01 (t, $J^{I}_{2,3}$=$J^{I}_{3,4}$=9.5 Hz, 1 H, H-3$^I$), 3.92 (d, J=14.5 Hz, 1 H, COCH$_2$Cl), 3.85 (d, J=14.5 Hz, 1 H, COCH$_2$Cl), 3.75 (dd, $J^{I}_{5,6_a}$=4.0 Hz, $J^{I}_{6_a,6_b}$=11.5 Hz, H-6$^I$a), 3.68 (m, 1 H, H-5$^{II}$), 3.67 (m, 1 H, H-5$^I$), 3.50 (dd, $J^{I}_{5,6_b}$=2.0 Hz, 1 H, H-6$^I$b), 3.46 (dd, 1 H, H-2$^I$), 3.44 (t, $J^{I}_{4,5}$=10.0 Hz, 1 H, H-4$^I$), 3.41 (dd, $J^{II}_{5,6_a}$=3.0 Hz, $J^{II}_{6_a,6_b}$=11.0 Hz, 1 H, H-6$^{II}$), 3.39 (s, 3 H, OCH$_3$), 3.36 (dd, $J^{II}_{5,6_b}$=3.5 Hz, 1 H, H-6$^{II}$b), 3.24 (dd, 1 H, H-2$^{II}$).

$^{13}$C NMR (125 MHz, CDCl$_3$) δ: 165.5 (COCH$_2$Cl), 158.0 (oxazolidinone, C=O), 138.5, 138.1, 137.8, 137.2, 134.6 (aromatic C), 129.0-127.7 (aromatic C), 98.3 (C-1$^I$), 95.6 (C-1$^{II}$), 82.0 (C-3$^I$), 79.6 (C-2$^I$), 77.0 (C-4$^I$), 75.8 (CH$_2$Ph), 74.8 (CH$_2$Ph), 73.6 (C-3$^{II}$), 73.5 (2 C, 2 CH$_2$Ph), 70.8 (C-5$^{II}$), 70.2 (C-4$^{II}$), 70.0 (C-5$^I$), 67.1 (C-6$^{II}$), 66.6 (C-6$^I$), 59.9 (C-2$^{II}$), 55.4 (OCH$_3$), 47.8 (N—CH$_2$Ph) 40.3 (COCH$_2$Cl).

β-Linked Disaccharide 8b: $[\alpha]^{26}_D$ +12 (c, 1.0, CHCl$_3$).

$^1$H NMR (500 MHz, CDCl$_3$) δ: 7.40-7.23 (25 H, aromatic H), 5.22 (dd, $J^{II}_{3,4}$$^{II}$=10.5 Hz, $J^{II}_{4,5}$$^{II}$=8.0 Hz, 1 H, H-4$^{II}$), 4.99 (d, J=11.0 Hz, 1 H, CH$_2$Ph), 4.80 (d, J=11.0 Hz, 1 H, CH$_2$Ph), 4.87 (d, J=11.5 Hz, 1 H, CH$_2$Ph), 4.52 (d, J=11.5 Hz, 1 H, CH$_2$Ph), 4.80 (d, J=11.5 Hz, 1 H, CH$_2$Ph), 4.62 (d, J=11.5 Hz, 1 H, CH$_2$Ph), 4.56 (d, J=15.0 Hz, 1 H, N—CH$_2$Ph), 4.27 (d, J=15.0 Hz, 1 H, N—CH$_2$Ph), 4.56 (d, $J^{I}_{1,2}$=3.0 Hz, 1 H, H-1$^I$), 4.49 (d, J=12.0 Hz, 1 H, CH$_2$Ph), 4.41 (d, J=12.0 Hz, 1 H, CH$_2$Ph), 4.40 (d, $J^{II}_{1,2}$$^{II}$=8.0 Hz, 1 H, H-1$^{II}$), 4.02 (t, $J^{I}_{3,4}$=10.0 Hz, 1 H, H-3$^I$), 4.01 (dd, $J^{I}_{5,6_a}$=10.5 Hz, $J^{I}_{6_a,6_b}$=12.5 Hz, 1 H, H-3$^{II}$), 4.00 (dd, $J^{II}_{2,3}$$^{II}$=12.0 Hz, 1 H, H-3$^{II}$), 3.93 (d, J=15.0 Hz, 1 H, COCH$_2$Cl), 3.85 (d, J=15.0 Hz, 1 H, COCH$_2$Cl), 3.84 (m, 1 H, H-5$^{II}$), 3.60 (dddd, 1 H, H-5$^{II}$), 3.54 (m, 2 H, H-6$^{II}$a and H-6$^{II}$b), 3.52 (dd, $J^{I}_{5,6}$=5.5 Hz, 1 H, H-6$^I$b), 3.47 (dd, $J^{I}_{2,3}$=9.5 Hz, 1 H, H-2$^I$), 3.34 (s, 3 H, OCH$_3$), 3.33 (t, 1 H, H-4$^I$), 3.30 (dd, 1 H, H-2$^{II}$).

$^3$C NMR (125 MHz, CDCl$_3$) δ: 165.7 (COCH$_2$Cl), 158.1 (oxazolidinone, C=O), 138.5, 138.1, 137.9, 137.3, 135.1 (aromatic C), 129.3-127.7 (aromatic C), 102.0 (C-1$^I$), 98.2 (C-1$^{II}$), 81.9 (C-3$^I$), 79.8 (C-2$^I$), 77.8 (C-4$^I$), 76.7 (C-3$^{II}$), 75.8 (CH$_2$Ph), 75.3 (C-5$^{II}$), 74.7 (CH$_2$Ph), 73.7 (CH$_2$Ph), 73.4 (CH$_2$Ph), 70.0 (C-4$^{II}$), 69.8 (C-5$^I$), 68.6 (C-6$^{II}$), 68.5 (C-6$^I$), 60.1 (C-2$^{II}$), 55.5 (OCH$_3$), 48.0 (N—CH$_2$Ph), 40.3 (COCH$_2$Cl).

Anal. Calcd for C$_{51}$H$_{54}$ClNO$_{12}$: C, 67.43; H, 5.99; N, 1.54. Found: C, 67.47; H, 5.89; N, 1.49

Also NIS-TMSOTf activation was performed. Compound 7 (23 mg, 0.050 mmol) and compound 5 (33 mg, 0.06 mmol) were dissolved in CH$_2$Cl$_2$ (3 ml), and the reaction was allowed to proceed in the presence of N-iodosuccinimide (20 mg, 0.089 mmol), TMSOTf (2 µl, 0.012 mmol), and MS (4 Å, 0.4 g) at room temperature for 1.5 hours. The subsequent work-up and purification by preparative TLC (toluene/hexane/ethylacetate, 4:1:1) gave compounds 8a (9 mg, 20%) and 8b (14 mg, 31%).

Further, Compound 7 (22 mg, 0.050 mmol) and compound 5 (32 mg, 0.06 mmol) were dissolved in CH$_2$Cl$_2$ (3 ml), and the reaction was allowed to proceed in the presence of dimethylmethylthio sulfonium triflate (mixed with SiO$_2$ 1.0 mmol/g, 0.29 g, 0.29 mmol), TMSOTf (2 µl, 0.012 mmol), and MS (4 Å, 0.3 g) at room temperature for 1.5 hours. The subsequent work-up and purification by preparative TLC (toluene/hexane/ethylacetate, 4:1:1) gave compounds 8a (13 mg, 30%) and 8b (21 mg, 48%).

(9) Methyl(N-benzyl-2-amino-4-O-acetyl-6-O-benzyl-2-N,3-O-carbonyl-2-deoxy-α- and β-D-galactopyranpsyl)-(1->4)-2,3,4-tri-O-benzyl-β-D-glucopyranoside (Compound 9a and Compound 9b)

Method C: Compound 7 (100 mg, 0.215 mmol) and compound 6 (134 mg, 0.258 mmol) were dissolved in 1,4-dioxane/toluene (3:1, 8 ml), and the reaction was allowed to proceed overnight in the presence of DTBMP (106 mg, 0.516 mmol), AgOTf (99 mg, 0.387 mmol), PhSCl (36 µl, 0.310 mmol), and MS (4 Å, 0.8 g) while heating the solution from 0° C. to room temperature. The subsequent work-up and purifications by gel permeation chromatography (SX-3) and flash column chromatography on silica gel (CHCl$_3$/toluene/ethylacetate, 7:2:1->4:1:1) gave compound 9a (143 mg, 76%) and compound 9b (9 mg, 5%).

α-Linked Disaccharide 9a:

$^1$H NMR (500 MHz, CDCl$_3$) δ: 7.37-7.17 (m, 25 H, aromatic H), 5.54 (br. s, 1 H, H-4$^{II}$), 5.01 (d, J=11.0 Hz, 1 H, CH$_2$Ph), 4.83 (d, J=11.0 Hz, 1 H, CH$_2$Ph), 4.90 (d, J=11.5 Hz, 1 H, CH$_2$Ph), 4.54 (d, J=11.5 Hz, 1 H, CH$_2$Ph), 4.79 (d, J=12.0 Hz, 1 H, CH$_2$Ph), 4.63 (d, J=12.0 Hz, 1 H, CH$_2$Ph), 4.75 (d, $J^{II}_{1,2}$$^{II}$=3.0 Hz, 1 H, H-1$^{II}$), 4.49 (d, $J^{I}_{1,2}$=3.5 Hz, 1 H, H-1$^I$), 4.47 (dd, $J^{II}_{2,3}$$^{II}$=12.0 Hz, $J^{II}_{3,4}$$^{II}$=3.0 Hz, 1 H, H-3$^{II}$), 4.58 (d, J=12.0 Hz, 1 H, CH$_2$Ph), 4.35 (d, J=12.0 Hz, 1 H, CH$_2$Ph), 4.45 (d, J=15.0 Hz, 1 H, N—CH$_2$Ph), 4.17 (d, J=15.0 Hz, 1 H, N—CH$_2$Ph), 4.00 (t, $J^{I}_{2,3}$=$J^{I}_{3,4}$=9.5 Hz, 1 H, H-3$^I$), 3.93 (br, t, 1 H, H-5$^{II}$), 3.67 (dd, $J^{I}_{5,6_a}$=5.0 Hz, $J^{II}_{6_a,6_b}$=10.5 Hz, 1 H, H-6$^I$a), 3.65 (m, 1 H, H-5$^{II}$), 3.59 (dd, 1 H), H-2$^{II}$), 3.45 (dd, 1 H, H-2$^I$), 3.41 (dd, $J^{I}_{5,6_b}$=1.5 Hz, 1 H, H-6$^I$b), 3.38 (d, $J^{II}_{5,6}$=5.5 Hz, 2 H, H-6$^{II}$a and H-6$^{II}$b), 3.38 (s, 3 H, OCH$_3$), 3.38 (t, $J^{I}_{4,5}$=9.5 Hz, 1 H, H-4$^I$), 1.97 (s, 3 H, COCH$_3$).

$^{13}$C NMR (125 MHz, CDCl$_3$) δ: 169.3 (COCH$_3$), 158.2 (oxazolidinone, C=O), 138.5, 138.1, 137.8, 137.4, 135.0, 128.8-127.6 (aromatic C), 98.1 (C-1$^I$), 96.4 (C-1$^{II}$), 82.0 (C-3$^I$), 79.6 (C-2$^I$), 77.3 (C-4$^I$), 75.8 (CH$_2$Ph), 74.8 (CH$_2$Ph), 73.5 (2 C, 2 CH$_2$Ph), 72.0 (C-3$^{II}$), 69.8 (C-5$^I$), 69.5 (C-5$^{II}$), 67.9 (C-6$^{II}$), 66.8 (C-6$^I$), 66.3 (C-4$^{II}$), 65.4 (C-2$^{II}$), 55.3 (OCH$_3$), 48.0 (N—CH$_2$Ph), 20.6 (COCH$_3$).

β-Linked Disaccharide 9b:

$^1$H NMR (500 MHz, CDCl$_3$) δ: 7.40-7.21 (m, 25 H, aromatic H), 5.56 (br. t, J$_{3,4}^{II}$=2.5 Hz, 1 H, H-4$^{II}$), 4.99 (d, J=11.0 Hz, 1 H, CH$_2$Ph), 4.79 (d, J=11.0 Hz, 1H, CH$_2$Ph), 4.83 (d, J=11.5 Hz, 1 H, CH$_2$Ph), 4.48 (d, J=11.5 Hz, 1 H, CH$_2$Ph), 4.79 (d, J=12.5 Hz, 1 H, CH$_2$Ph), 4.62 (d, J=12.5 Hz, 1 H, CH$_2$Ph), 4.55 (d, J$_{1,2}^I$=4.0 Hz, 1 H, H-1$^I$), 4.53 (d, J=1.50 Hz, 1 H, N—CH$_2$Ph), 4.33 (d, J=15.0 Hz, 1 H, N—CH$_2$Ph), 4.49 (d, J=12.0 Hz, 1 H, CH$_2$Ph), 4.40 (d, J=12.0 Hz, 1 H, CH$_2$Ph), 4.33 (d, J$_{1,2}^{II}$=8.0 Hz, 1 H, H-1$^{II}$), 4.00 (t, J$_{2,3}^I$=J$_{3,4}^I$=9.5 Hz, 1 H, H-3$^I$), 4.00 (dd, J$_{2,3}^{II}$=12.0 Hz, 1 H, H-3$^{II}$), 3.98 (dd, J$_{5,6a}^I$=2.0 Hz, J$_{6a,6b}^I$=10.5 Hz, 1H, H-6a), 3.83 (dddd, J$_{4,5}^I$=10.0 Hz, J$_{5,6b}^I$=5.5 Hz, 1 H, H-5$^I$), 3.81 (ddd, J$_{4,5}^{II}$=1.0 Hz, 1 H, H-5$^{II}$), 3.58 (dd, 1 H, H-2$^{II}$), 3.48 (m, 1 H, H-6$^I$b), 3.48 (m, 2 H, H-6$^{II}$a and H-6$^{II}$b), 3.47 (m, 1 H, H-2$^I$), 3.33 (s, 3 H, OCH$_3$), 3.32 (dd, 1 H, H-4$^I$).

$^{13}$C NMR (125 MHz, CDCl$_3$) δ: 169.1 (COCH$_3$), 158.3 (oxazolidinone, C=O), 138.5, 138.1, 138.0, 137.4, 135.7, 129.0-127.9 (aromatic C), 102.8 (C-1$^{II}$), 98.1 (C-1$^I$), 81.9 (C-3$^I$), 79.8 (C-2$^I$), 77.9 (C-4$^I$), 76.4 (C-3$^{II}$), 75.8 (CH$_2$Ph), 74.7 (CH$_2$Ph), 74.3 (C-5$^{II}$), 73.7 (CH$_2$Ph), 73.4 (CH$_2$Ph), 69.7 (C-5$^I$), 68.4 (C-6$^I$), 67.5 (C-6$^{II}$), 64.7 (C-4$^{II}$), 57.5 (C-2$^{II}$), 57.5 (C-2$^{II}$), 55.5 (OCH$_3$), 48.3 (N—CH$_2$Ph), 20.5 (COCH$_3$).

(10) Methyl(N-benzyl-2-amino-2-N,3-O-carbonyl-4-O-chloroacetyl-2-deoxy-α-D-glucopyranpsyl)-(1->4)-2,3,4-tri-O-benzoyl-α-D-glucopyranoside (Compound 11)

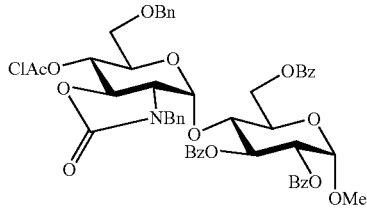

Method B: Compound 5 (34 mg, 0.061 mmol) was allowed to react with Compound 10 (26 mg, 0.051 mmol) in the presence of N-(phenylthio)-ε-caprolactam (15 mg, 0.067 mmol), Tf$_2$O (12 μl, 0.073 mmol) and MS (4 Å, 0.3 g) at room temperature for 30 minutes in CH$_2$Cl$_2$ (3 ml). The subsequent work-up and purification by preparative TLC (CHCl$_3$/ethylacetate, 19:1) gave compound 11 (25 mg, 52%).

[α]$^{26}$$_D$+132 (c, 1.0, CHCl$_3$).

$^1$H NMR (500 MHz, CDCl$_3$) δ: 8.11-7.01 (m, 25 H, aromatic H), 6.14 (dd, J$_{2,3}^I$=10.0 Hz, J$_{4,5}^I$=9.0 Hz, 1 H, H-3$^I$), 5.32 (d, J$_{1,2}^{II}$=3.5 Hz, 1 H, H-1$^{II}$), 5.26 (t, J$_{4,5}^{II}$=10.0 Hz, 1 H, H-4$^{II}$), 5.26 (dd, J$_{1,2}^I$=3.5 Hz, 1 H, H-2$^I$), 5.15 (d, 1 H, H-1$^I$) 4.76 (dd, J$_{5,6a}^I$=2.0 Hz, J$_{6a,6b}^I$=12.5 Hz, 1 H, H-6$^I$a), 4.60 (dd, J$_{5,6b}^I$=3.5 Hz, 1 H, H-6$^I$b), 4.52 (dd, J$_{2,3}^{II}$=12.0 Hz, J$_{3,4}^{II}$=10.5 Hz, 1 H, H-3$^{II}$), 4.50 (d, J=15.0 Hz, 1 H, N—CH$_2$Ph), 3.64 (d, J=15.0 Hz, 1 H, N—CH$_2$Ph), 4.41 (d, J=12.0 Hz, 1 H, CH$_2$Ph), 4.20 (d, J=12.0 Hz, 1 H, CH$_2$Ph), 4.37 (t, J$_{4,5}^I$=9.5 Hz, 1 H, H-4$^I$), 4.23 (m, 1 H, H-5$^I$), 3.92 (d, J=14.5 Hz, 1 H, COCH$_2$Cl), 3.79 (d, J=14.5 Hz, 1 H, COCH$_2$Cl), 3.47 (s, 3 H, OCH$_3$), 3.30 (dd, J$_{5,6a}^{II}$=2.0 Hz, J$_{6a,6b}^{II}$=11.0 Hz, 1 H, H-6$^{II}$a), 3.20 (dd, J$_{5,6b}^{II}$=3.5 Hz, 1 H, H-6$^{II}$b), 3.13 (dd, 1 H, H-2$^{II}$).

$^{13}$C NMR (125 MHz, CDCl$_3$) δ: 166.0 (COPh), 165.9 (COPh), 165.9 (COPh), 165.5 (COCH$_2$Cl), 157.7 (oxazolidinone, C=O), 136.9, 134.0,133.8, 133.5, 129.9-127.9 (aromatic C), 96.8 (C-1$^I$), 94.6 (C-1$^{II}$), 73.5 (CH$_2$Ph), 73.4 (C-4$^I$), 73.0 (C-3$^{II}$), 72.6 (C-3$^I$), 72.3 (C-5$^{II}$), 71.9 (C-2$^I$), 69.8 (C-4$^{II}$), 68.1 (C-5$^I$), 66.8 (C-6$^{II}$), 59.0 (C-2$^I$), 55.7 (OCH$_3$), 47.1 (N—CH$_2$Ph), 40.3 (COCH$_2$Cl).

(11) p-Methoxyphenyl(N-benzyl-2-amino-2-N,3-O-carbonyl-4-O-chloroacetyl-2-deoxy-α-D-glucopyranpsyl)-(1->4)-3,6-di-O-benzyl-2-deoxy-2-phthalimide-β-D-glucopyranpside (Compound 13)

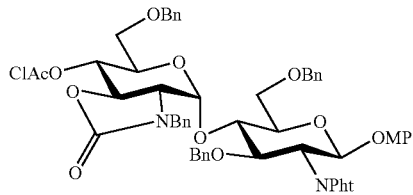

Method B: Compound 12 (27 mg, 0.045 mmol) and compound 5 (30 mg, 0.054 mmol) were dissolved in CH$_2$C$_{12}$ (3 ml), the reaction was allowed to proceed in the presence of N-(phenylthio)-ε-caprolactam (13 mg, 0.059 mmol), Tf$_2$O (11 μl, 0.065 mmol), and MS (4 Å, 0.3 g) at room temperature for 40 minutes. The subsequent work-up and purification by preparative TLC (toluene/hexane/ethylacetate, 4:1:1) gave compound 13 (26 mg, 56%).

[α]$^{26D}$+69 (c, 0.5, CHCl$_3$)

$^1$H NMR (500 MHz, CDCl$_3$) δ: 7.44-7.00 (m, 29 H, aromatic H), 5.60 (d, J$_{1,2}^I$=8.5 Hz, 1 H, H-1$^I$), 5.49 (d, J$_{1,2}^{II}$=3.0 Hz, 1 H, H-1$^{II}$), 5.32 (t, J$_{4,5}^{II}$=10.0 Hz, 1 H, H-5$^{II}$), 4.73 (d, J=12.0 Hz, 1 H, CH$_2$Ph), 4.36 (d, J=12.0 Hz, 1 H, CH$_2$Ph), 4.64 (d, J=14.5 Hz, 1 H, N—CH$_2$Ph), 4.00 (d, J=14.5 Hz, 1 H, N—CH$_2$Ph), 4.60 (d, J=11.5 Hz, 1 H, CH$_2$Ph), 4.55 (d, J=11.5 Hz, 1 H, CH$_2$Ph), 4.59 (dd, J$_{2,3}^{II}$=12.0 Hz, J$_{3,4}^{II}$=10.5 Hz, 1 H, H-3$^{II}$), 4.58 (t, J$_{2,3}^I$=9.0 Hz, 1 H, H-2$^I$), 4.54 (t, J$_{3,4}^I$=9.0 Hz, 1 H, H-3$^I$), 4.50 (d, J=11.5 Hz, 1 H, CH$_2$Ph), 4.36 (d, J=11.5 Hz, 1 H, CH$_2$Ph), 4.26 (t, J$_{4,5}^I$=9.0 Hz, 1 H, H-4$^I$), 4.05 (dd, J$_{5,6a}^I$=3.0 Hz, J$_{6a,6b}^I$=11.5 Hz, 1 H, H-6$^I$a), 4.01 (m, 1 H, H-5$^I$), 3.96 (d, J=15.0 Hz, 1 H, COCH$_2$Cl), 3.88 (d, J=15.0 Hz, 1 H, COCH$_2$Cl), 3.79 (dd, J$_{5,6b}^I$=1.5 Hz, 1 H, H-6$^I$b), 3.71 (s, 3 H, PhOCH$_3$), 3.41 (dd, J$_{5,6a}^{II}$=2.5 Hz, J$_{6a,6b}^{II}$=11.0 Hz, 1 H, H-6$^{II}$a), 3.36 (dd, J$_{5,6b}^{II}$=4.0 Hz, 1 H, H-6$^{II}$b).

$^{13}$C NMR (125 MHz, CDCl$_3$) δ: 165.6 (COCH$_2$Cl), 157.9 (oxazolidinone, C=O), 155.5, 150.7 (phthalimide, C=O), 138.0, 137.2, 134.2, 134, 131.4, 129.1-127.4, 123.5, 118.9, 114.4 (aromatic C), 97.8 (C-1$^I$), 95.5 (C-1$^{II}$), 79.1 (C-3$^I$), 76.5 (C-4$^I$), 74.9 (C-5$^I$), 73.5 (CH$_2$Ph), 73.5 (C-3$^{II}$), 73.4 (CH$_2$Ph), 73.2 (CH$_2$Ph), 71.8 (C-5$^{II}$), 70.4 (C-4$^{II}$), 68.6 (C-6$^I$), 67.6 (C-6$^{II}$), 59.9 (C-2$^{II}$), 55.6 (OCH$_3$), 55.0 (C-2$^I$), 47.7 (N—CH$_2$Ph), 40.4 (COCH$_2$Cl).

(12) N-benzyl-2-amino-6-O-benzyl-2,3-N,O-carbonyl-4-O-chloroacetyl-2-deoxy-α- and β-D-glucopyranosyl -(1->4)-methyl 3-O-benzyl-1,2-isopropylidene-β-L-Idopyranosiduronate (Compound 15a and Compound 15b)

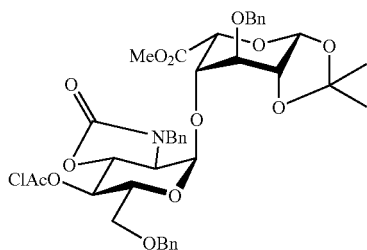

Method B: Compound 14 (24 mg, 0.071 mmol) and Compound 5 (47 mg, 0.085 mmol) were dissolved in CH$_2$Cl$_2$ (3 ml), the reaction was allowed to proceed in the presence of DTBMP (35 mg, 0.170 mmol), N-(phenylthio)-ε-caprolactam (21 mg, 0.093 mmol), Tf$_2$O (14 μl, 0.085 mmol), and MS (4 Å, 0.3 g) for 30 minutes. The subsequent work-up and purification by gel permeation chromatography (SX-3, toluene) and flash column chromatography on silica gel (CHCl$_3$/ethylacetate, 10:1) gave compound 15a (35 mg, 63%) and compound 15b (2 mg, 4%).

Method C: Compound 14 (25 mg, 0.074 mmol) and Compound 5 (65 mg, 0.118 mmol) were dissolved in toluene-dioxane (3:1, 3 ml), and the reaction was allowed to proceed overnight in the presence of DTBMP (48 mg, 0.236 mmol), AgOTf (45 mg, 0.177 mmol), PhSCl (16 μl, 0.142 mmol), and MS (4 Å, 0.3 g) at a temperature between 0° C. and room temperature. The subsequent work-up and purifications by gel permeation chromatography (SX-3, toluene) and flash column chromatography on silica gel (CHCl$_3$/ethylacetate, 10:1) gave compound 15a (44 mg, 71%).

α-Linked Disaccharide 15a: $[\alpha]^{26}_D$ +8 (c, 1.0, CHCl$_3$).

$^1$H NMR (500 MHz, CDCl$_3$) δ: 7.44-7.10 (m, 15 H, aromatic H), 5.39 (t, $J_{3,4}^{II}$=$J_{4,5}^{II}$=10.0 Hz, 1 H, H-4$^{II}$), 5.37 (d, $J_{1,2}^{I}$=2.5 Hz, 1 H, H-1$^{I}$), 4.91 (d, $J_{1,2}^{II}$=3.0 Hz, 1 H, H-1$^{II}$), 4.75 (d, J=15.0 Hz, 1 H, N—CH$_2$Ph), 3.99 (d, J=15.0 Hz, 1 H, N—CH$_2$Ph), 4.70 (d, J=12.0 Hz, 1 H, CH$_2$Ph), 4.67 (d, J=12.0 Hz, 1 H, CH$_2$Ph), 4.58 (d, J=11.5 Hz, 1 H, CH$_2$Ph), 4.37 (d, J=11.5 Hz, 1 H, CH$_2$Ph), 4.48 (dd, $J_{2,3}^{II}$=12.0 Hz, 1 H, H-3$^{II}$), 4.48 (d, $J_{4,5}^{I}$=1.5 Hz, 1 H, H-5$^{I}$), 4.10 (t, $J_{2,3}^{I}$=$J_{3,4}^{I}$=2.5 Hz, 1 H, H-3$^{I}$), 3.88 (d, J=15.0 Hz, 1 H, COCH$_2$Cl), 3.82 (d, J=15.0 Hz, 1 H, COCH$_2$Cl), 3.74 (s, 3 H, CO$_2$CH$_3$), 3.73 (m, 1 H, H-5$^{II}$), 3.54 (dd, $J_{5,6_a}^{II}$=3.0 Hz, $J_{6_a,6_b}^{II}$=11.0 Hz, 1 H, H-6$^{II}$a), 3.42 (dd, $J_{5,6_b}^{II}$=3.5 Hz, 1 H, H-6$^{II}$b), 3.26 (dd, 1 H, H-2$^{II}$), 1.57 [s, 3 H, C(CH$_3$)$_2$] 1.40 [s, 3 H, C(CH$_3$)$_2$].

$^{13}$C NMR (125 MHz, CDCl$_3$) δ: 169.2 (C-6$^{I}$), 165.4 (COCH$_2$Cl), 157.8 (oxazolidinone, C=O), 137.1, 136.5, 134.6, 129.1, 128.8, 128.6, 128.5, 128.5, 128.4, 128.2, 128.0, 127.8 (aromatic C), 112.4 [C(CH$_3$)$_2$], 96.7 (C-1$^{I}$), 93.2 (C-1$^{I}$), 74.7 (C-2$^{I}$), 73.6 (C-3$^{II}$), 73.5 (CH$_2$Ph), 72.4 (CH$_2$Ph), 71.4 (C-5$^{II}$), 71.1 (C-4$^{I}$), 71.0 (C-5$^{I}$), 71.0 (C-3$^{I}$), 69.8 (C-4$^{II}$), 66.5 (C-6$^{II}$), 58.9 (C-2$^{II}$), 52.6 (CO$_2$CH$_3$), 47.1 (N—CH$_2$Ph), 40.3 (COCH$_2$Cl), 28.0 [C(CH$_3$)$_2$], 26.2 [C(CH$_3$)$_2$].

β-Linked Disaccharide 15b:

$^1$H NMR (500 MHz, CDCl$_3$) δ: 7.41-7.21 (m, 15 H, aromatic H), 5.30 (d, $J_{1,2}^{I}$=2.0 Hz, 1 H, H-1$^{I}$), 5.24 (dd, $J_{3,4}^{I}$=10.5 Hz, $J_{4,5}^{II}$=9.0 Hz, 1 H, H-4$^{II}$), 4.84 (d, $J_{1,2}^{II}$=8.0 Hz, 1 H, H-1$^{II}$), 4.60 (d, J=15.0 Hz, 1 H, N—CH$_2$Ph), 4.15 (d, J=15.0 Hz, 1 H, N—CH$_2$Ph), 4.57 (d, J=11.5 Hz, 1 H, CH$_2$Ph), 4.54 (d, J=11.5 Hz, 1 H, CH$_2$Ph), 4.48 (d, J=12.0 Hz, 1 H, CH$_2$Ph), 4.44 (d, J=12.0 Hz, 1 H, CH$_2$Ph), 4.46 (m, 1 H, H-5$^{I}$), 4.36 (t, $J_{2,3}^{I}$=$J_{3,3}^{I}$=2.0 Hz, 1 H, H-1$^{I}$), 4.18 (br. s, 1 H, H-4$^{I}$), 4.08 (dd, $J_{2,3}^{II}$=12.0 Hz, 1 H, H-3$^{II}$), 3.98 (d, J=15.0 Hz, 1 H, COCH$_2$Cl), 3.92 (d, J=15.0 Hz, 1 H, COCH$_2$Cl), 3.94 (br. s, 1 H, H-2$^{I}$), 3.74 (m, 1 H, H-5$^{II}$), 3.70 (s, 3 H, CO$_2$CH$_3$), 3.58 (dd, $J_{5,6_a}^{II}$=5.5 Hz, $J_{6_a,6_b}^{II}$=10.5 Hz, 1 H, H-6$^{II}$a), 3.46 (dd, $J_{5,6_b}^{II}$=2.5 Hz, 1 H, H-6$^{II}$b), 1.44 [s, 3H, C(CH$_3$)$_2$], 1.38 [s, 3 H, C(CH$_3$)$_2$].

(13) N-benzyl-2-amino-6-O-benzyl-2,3-N,O-carbonyl-4-O-chloroacetyl-2-deoxy-α- and β-D-glucopyranosyl (1->4)-methyl 3-O-benzyl-1,2-isopropylidene-α-D-glucopyranosiduronate (Compound 17a and Compound 17b)

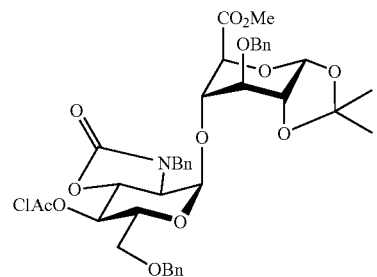

Method C: Compound 16 (81 mg, 0.239 mmol) was allowed to react with compound 5 (159 mg, 0.287 mmol) in 1,4-dioxane/toluene (3:1, 8 ml) in the presence of DTBMP (118 mg, 0.574 mmol), AgOTf (111 mg, 0.431 mmol), PhSCl (40 μl, 0.344 mmol), and MS (4 Å, 0.8 g) at a temperature between 0° C. and room temperature. The subsequent work-up and purifications by gel permeation chromatography (SX-3, toluene) and flash column chromatography on silica gel (CHCl$_3$/ethylacetate, 14:1->12:1) gave compound 17a (135 mg, 71%) and compound 17b (7 mg, 4%).

α-Linked disaccharide 17a: $[\alpha]^{26}_D$ +52 (c, 1.0, CHCl$_3$).

$^1$H NMR (500 MHz, CDCl$_3$) δ: 7.34-7.10 (15 H, aromatic H), 5.79 (d, $J_{1,2}^{I}$=4.0 Hz, 1 H, H-1$^{I}$), 5.39 (t, $J_{3,4}^{II}$=$J_{4,5}^{II}$=10.0 Hz, 1 H, H-4$^{II}$), 5.10 (d, $J_{1,2}^{II}$=3.0 Hz, 1 H, H-1$^{II}$), 4.64 (d, J=12.0 Hz, 1 H each, CH$_2$Ph), 4.55 (d, J=12.0 Hz, 1 H each, CH$_2$Ph), 4.61 (d, J=15.0 Hz, 1H, N—CH$_2$Ph), 4.02 (d, J=15.0 Hz, 1H, N—CH$_2$Ph), 4.58 (dd, $J_{2,3}^{II}$=12.0 Hz, 1 H, H-3$^{II}$), 4.57 (d, J=11.5 Hz, 1 H, CH$_2$Ph), 4.38 (d, J=11.5 Hz, 1 H, CH$_2$Ph), 4.53 (d, $J_{4,5}^{I}$=5.5 Hz, 1 H, H-5$^{I}$), 4.21 (t, $J_{2,3}^{I}$=4.0 Hz, 1 H, H-2$^{I}$), 4.16 (dd, $J_{3,4}^{I}$=4.0 Hz, 1 H, H-4$^{I}$), 3.92 (dddd, $J_{5,6_a}^{II}$=2.5 Hz, $J_{5,6_b}^{II}$=3.5 Hz, 1 H, H-5$^{II}$), 3.91 (d, J=15.0 Hz, 1 H, COCH$_2$Cl), 3.84 (d, J=15.0 Hz, 1 H, COCH$_2$Cl), 3.82 (t, 1 H, H-3$^{I}$), 3.65 (s, 3 H, CO$_2$CH$_3$), 3.53 (dd, $J_{6_a,6_b}^{II}$=11.0 Hz, 1 H, H-6$^{II}$a), 3.46 (dd, 1 H, H-6$^{II}$b), 3.33 (dd, 1 H, H-2$^{II}$), 1.58, [s, 3 H, C(CH$_3$)$_2$], 1.38 [s, 3 H, C(CH$_3$)$_2$]. $^{13}$C NMR (125 MHz, CDCl$_3$) δ: 169.8 (C-6$^{I}$), 165.5 (COCH$_2$Cl), 157.9 (oxazolidinone, C=O), 137.1, 136.9, 134.6, 129.0, 128.6, 128.5, 128.3, 128.2, 128.1, 127.9, 127.5 (aromatic C), 111.1 [C(CH$_3$)$_2$], 95.5 (C-1$^{I}$), 94.2 (C-1$^{II}$), 75.1 (C-2$^{I}$), 74.5 (C-3$^{I}$), 73.6 (C-3$^{II}$), 73.5 (CH$_2$Ph), 72.5 (C-4$^{I}$), 71.9 (C-5$^{I}$), 71.8 (CH$_2$Ph), 71.6 (C-5$^{II}$), 67.0 (C-4$^{II}$), 66.9 (C-6$^{II}$), 59.7 (C-2$^{II}$), 52.4 (CO$_2$CH$_3$), 47.6 (N—CH$_2$Ph), 40.3 (COCH$_2$Cl), 27.3 [C(CH$_3$)$_2$], 25.8 [C(CH$_3$)$_2$].

(14) Methyl(2-acetamide-3,4,6-tri-O-acetyl-α-D-glucopyranosyl)-(1->6)-2,3,4-tri-O-acetyl-α-D-glucopyranoside (Compound 18)

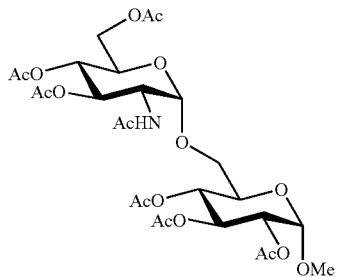

Compound 8 (64 mg, 0.07 mmol) was treated with 1 M aqueous NaOH/1,4-dioxane (1:1, v/v, 8 mL) at 40° C. for 2 days. The mixture was diluted with ethyl acetate and washed with water. The separated aqueous layer was extracted with ethylacetate. The combined organic extracts were washed with water and brine, dried (Na$_2$SO$_4$), filtered and concentrated. The residue was dissolved in 1,4-dioxane/water (2:1, 4.5 mL) containing 90 μL of 0.1 M aqueous HCl (2% of the volume of the solvent) and 20% Pd(OH)$_2$/C (30 mg) was added. The mixture was hydrogenated under an atmospheric pressure of hydrogen. After stirring for 12 hours 1.5 mL of water was added. The mixture was warmed to 50° C., hydrogenated for further 2 days, then filtered through a syringe filter (Millipore Millex LG, hydrophilic PTFE 0.2 μm cartridge) and the cartridge was washed with methanol and water. The filtrates were concentrated in vacuo. The residue was acetylated with pyridine/Ac$_2$O (2:1, v/v, 3 mL) at room temperature overnight, concentrated with toluene and purified by flash column chromatography on silica gel (4:1, ethylacetate/CHCl$_3$) to give compound 18 (42 mg, 92%) as a colorless foam.

$[\alpha]^{26}_D$ +147 (c 1.0, CHCl$_3$).

$^1$H NMR (500 MHz, CDCl$_3$): δ=6.26 (d, $J_{NH,H\text{-}2}{}^{II}$=9.5 Hz, 1 H, NHCOCH$_3$), 5.48 (t, $J_{2,3}^{I}$=$J_{3,4}^{I}$=10.0 Hz, 1 H, H-3$^I$), 5.20 (t, $J_{2,3}^{II}$=$J_{3,4}^{II}$=9.5 Hz, 1 H, H-3$^{II}$), 5.15 (t, $J_{4,5}^{I}$=10.0 Hz, 1 H, H-4$^I$), 5.12 (t, $J_{4,5}^{II}$=10.0 Hz, 1 H, H-4$^{II}$), 5.06 (d, $J_{1,2}^{II}$=3.5 Hz, 1 H, H-1$^{II}$), 4.92 (d, $J_{1,2}^{I}$=4.0 Hz, 1 H, H-1$^I$), 4.79 (dd, 1 H, H-2$^I$), 4.40 (dddd, 1 H, H-2$^{II}$), 4.22 (dd, $J_{5,6a}^{II}$=4.5 Hz, $J_{6a,6b}^{II}$=12.5 Hz, 1 H, H-6$^{II}$a), 4.10 (dd, $J_{5,6b}^{II}$=2.5 Hz, 1 H, H-6$^{II}$b), 3.98 (m, 1 H, H-5$^{II}$), 3.97 (m, 1 H, H-5$^I$), 3.76 (dd, $J_{5,6a}^{I}$=2.0 Hz, $J_{6a,6b}^{I}$=12.5 Hz, 1 H, H-6$^I$a), 3.72 (dd, $J_{5,6b}^{I}$=4.0 Hz, 1 H, H-6$^I$b), 3.41 (s, 3 H, OCH$_3$), 2.10 (s, 3 H, COCH$_3$), 2.09 (s, 3 H, COCH$_3$), 2.08 (s, 3 H, COCH$_3$), 2.04 (s, 3 H, COCH$_3$), 2.02 (s, 6 H, 2 COCH$_3$), 2.00 (s, 3 H, COCH$_3$).

$^{13}$C NMR (125 MHz, CDCl$_3$) δ: 171.1 (COCH$_3$), 170.6 (COCH$_3$), 170.2 (oxazolidinone, C=O), 170.0 (COCH$_3$), 169.9 (COCH$_3$), 169.9 (COCH$_3$), 169.3 (COCH$_3$), 97.0 (C-1$^{II}$), 96.7 (C-1$^I$), 71.0 (C-3$^{II}$), 70.9 (C-3$^I$), 70.2 (C-3$^I$), 68.5 (C-4$^I$), 68.4 (C-5$^I$), 68.0 (C-4$^{II}$), 67.9 (C-5$^{II}$), 64.3 (C-6$^I$), 61.9 (C-6$^{II}$), 55.5 (OCH$_3$), 51.5 (C-2$^{II}$), 22.8 (COCH$_3$), 20.7-20.6 (COCH$_3$).

Effects of the Invention

The present invention provides a novel compound that is useful as a sugar donor in the 1,2-cis-glycosylation reaction.

More specifically, the compound of the present invention is a sugar donor having high stereoselectivity in the glycosylation reaction. The compound of the present invention can be synthesized in a simple manner at a large scale. The expression of stereoselectivity in the glycosylation reaction does not require significantly low temperature conditions. The deprotection reaction can be carried out under basic conditions and the subsequent catalytic reductions.

The compound of the present invention is an improvement over conventional azido sugars in terms of the synthesis of raw materials and stereoselectivity. In the case of sugar donors using, as amino-protecting groups, conventional acetamide groups (Kerns et al.), deprotection of trans-oxazolidinone at 2,3-positions creates problems under basic conditions. Specifically, hydrolysis of the trans-oxazolidinone is intended to take place while maintaining acetamide groups; however, hydrolysis of the trans-oxazolidinone disadvantageously competes with hydrolysis of acetamide groups. Thus, selective hydrolysis is difficult to perform and various products are disadvantageously generated. In the case of the compound according to the present invention, trans-oxazolidinone is solely hydrolyzed among N-benzyl groups under basic conditions. Thus, the compound according to the present invention is free from such drawback.

Use of the compound of the present invention enables solid-phase synthesis as well as liquid-phase synthesis, sugar chain synthesis with the use of a soluble polymer carrier, or synthesis of a sugar chain comprising a 1,2-cis bond with the use of an automatic sugar chain synthesizer. Since amino sugars having 1,2-cis glycoside bonds are often observed in physiologically active sugar chains, such as heparin, GPI anchors or anti-*Helicobacter pylori* oligosaccharides as pharmaceutical products, the compound of the present invention is also useful for synthesizing such sugar chains.

The invention claimed is:

1. A compound represented by the following formula (1):

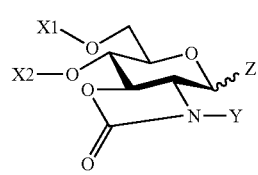

(1)

wherein X1 and X2 each independently represent a hydrogen atom or a hydroxyl-protecting group; Y represents a benzyl group or p-methoxy benzyl group; and Z represents —SC$_6$H$_5$.

2. The compound of claim 1 wherein Y represents a p-methoxy benzyl group.

3. The compound of claim 1 wherein X1 represents a benzyl group, p-methoxy benzyl group, benzoyl group, allyl group, or acetyl group, and X2 represents a chloroacetyl group.

4. A sugar-donating reagent for sugar chain synthesis which comprises the compound of claim 1.

5. A method for the synthesis of a sugar chain which comprises reacting the compound of claim 1 with a sugar acceptor.

* * * * *